United States Patent
Tamiya

(10) Patent No.: US 10,863,885 B2
(45) Date of Patent: Dec. 15, 2020

(54) ENDOSCOPE SYSTEM AND ILLUMINATION DEVICE

(71) Applicant: OLYMPUS CORPORATION, Hachioji (JP)

(72) Inventor: Kosei Tamiya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 15/837,252

(22) Filed: Dec. 11, 2017

(65) Prior Publication Data
US 2018/0098686 A1 Apr. 12, 2018

Related U.S. Application Data

(63) Continuation of application No. PCT/JP2015/067663, filed on Jun. 18, 2015.

(51) Int. Cl.
*A61B 1/00* (2006.01)
*G02B 23/24* (2006.01)
(Continued)

(52) U.S. Cl.
CPC ...... *A61B 1/00096* (2013.01); *A61B 1/00006* (2013.01); *A61B 1/0008* (2013.01);
(Continued)

(58) Field of Classification Search
None
See application file for complete search history.

(56) References Cited

U.S. PATENT DOCUMENTS

| 5,434,669 A | * | 7/1995 | Tabata | A61B 1/042 356/241.5 |
| 6,438,302 B1 | * | 8/2002 | Utsui | A61B 1/0638 385/116 |

(Continued)

FOREIGN PATENT DOCUMENTS

| EP | 2 263 520 A1 | 12/2010 |
| JP | 52-71888 A | 6/1977 |

(Continued)

OTHER PUBLICATIONS

Office Action dated Jul. 16, 2019, issued in counterpart JP Application No. 2017-524245, with English translation (9 pages).
(Continued)

*Primary Examiner* — Timothy J Neal
(74) *Attorney, Agent, or Firm* — Westerman, Hattori, Daniels & Adrian, LLP

(57) ABSTRACT

An endoscope system of the present invention is provided with: a long, thin inserted portion that includes an illuminating portion that emits an illumination light beam toward an imaging subject, an image-acquisition portion that acquires an image of the imaging subject, and a channel; and an illumination device that is disposed in the channel, wherein the illumination device includes an illuminating portion that emits, toward the imaging subject, an illumination light beam that has a divergence angle that is smaller than that of the illumination light beam and for which the image-acquisition portion has sensitivity, and a pulling member that extends to outside the channel from a base end of the illuminating portion, and wherein the illuminating portion can be removed from the channel by pulling the pulling member.

17 Claims, 6 Drawing Sheets

(51) Int. Cl.
  *A61B 1/005* (2006.01)
  *A61B 1/012* (2006.01)
  *A61B 1/06* (2006.01)
  *A61B 1/05* (2006.01)

(52) U.S. Cl.
  CPC ........ *A61B 1/00009* (2013.01); *A61B 1/0057* (2013.01); *A61B 1/00188* (2013.01); *A61B 1/012* (2013.01); *A61B 1/0638* (2013.01); *A61B 1/0676* (2013.01); *G02B 23/2423* (2013.01); *G02B 23/2461* (2013.01); *A61B 1/05* (2013.01)

(56) References Cited

U.S. PATENT DOCUMENTS

| | | | |
|---|---|---|---|
| 2004/0186351 A1* | 9/2004 | Imaizumi | A61B 1/00009 600/160 |
| 2010/0324366 A1 | 12/2010 | Shimotsu | |
| 2012/0157979 A1* | 6/2012 | Li | A61B 18/24 606/15 |

FOREIGN PATENT DOCUMENTS

| | | |
|---|---|---|
| JP | 5-297288 A | 11/1993 |
| JP | 2004-8381 A | 1/2004 |
| JP | 2004-121546 A | 4/2004 |
| JP | 2009-198241 A | 9/2009 |
| JP | 2011-258 A | 1/2011 |
| JP | 2011-36552 A | 2/2011 |
| JP | 2013-387 A | 1/2013 |
| JP | 2013-228798 A | 11/2013 |
| JP | 2015-39503 A | 3/2015 |

OTHER PUBLICATIONS

International Search Report dated Jul. 21, 2015, issued in Counterpart of International Application No. PCT/JP2015/067663 w/English Translation (4 pages).

* cited by examiner

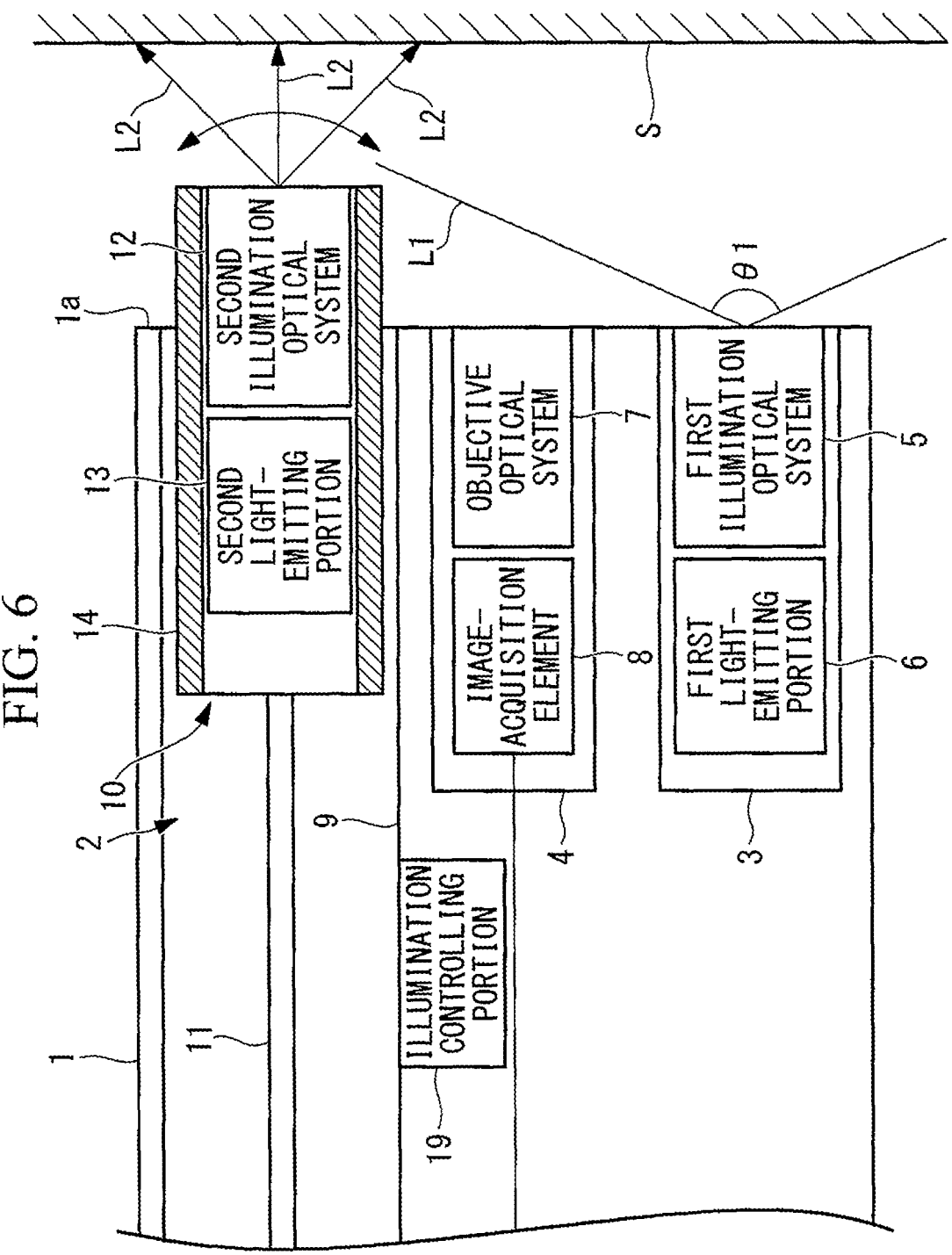

ENDOSCOPE SYSTEM AND ILLUMINATION DEVICE

CROSS-REFERENCE TO RELATED APPLICATIONS

This is a continuation of International Application PCT/JP2015/067663, with an international filing date of Jun. 18, 2015, which is hereby incorporated by reference herein in its entirety.

TECHNICAL FIELD

The present invention relates to an endoscope system and an illumination device.

BACKGROUND ART

In the related art, there is a known endoscope provided with a narrow-angle illumination system and a wide-angle illumination system (for example, see Patent Literature 1). When inserting the endoscope into a body, it is important to gain a sense of distance from the distal end of the endoscope to a far imaaing subject. Because an illumination light beam emitted from the narrow-angle illumination system has a smaller divergence angle as compared to an illumination light beam emitted from the wide-angle illumination system, it is possible to reach a farther imaging subject. Therefore, by using the narrow-angle illumination light beam, it is possible to acquire information about the distance to the far imaging subject.

CITATION LIST

Patent Literature (Patent Literature 1) Japanese Unexamined Patent Application, Publication No. Hei 5-297288

Solution to Problem

A first aspect of the present invention is an endoscope system including: a long, thin inserted portion that includes a first illuminating portion that emits a first illumination light beam toward an imaging subject, an image-acquisition portion that acquires an image of the imaging subject, and a channel that passes therethrough in a longitudinal direction; and an illumination device that includes a second illuminating portion that is disposed in the channel and that emits a second illumination light beam toward the imaging subject, and a long, thin pulling member that is connected to a base end of the second illuminating portion and that extends to outside from a base end of the channel, wherein the second illuminating portion is provided in such a way that the second illuminating portion can be removed from the channel by pulling the pulling member, and emits the second illumination light beam, which has a divergence angle that is smaller than that of the first illumination light beam and for which the image-acquisition portion has sensitivity.

In the above-described first aspect, the second illumination light beam may be visible light.

In the above-described first aspect, the second illumination light beam may be non-visible light.

In the above-described first aspect, the second illumination light beam may be diverging light that spreads out in a substantially right-circular-cone shape, and the endoscope system may be provided with an observation-distance calculating portion that calculates an observation distance from a distal end of the inserted portion to the imaging subject on the basis of the size of an area illuminated by the second illumination light beam in the image acquired by the image-acquisition portion.

In the above-described first aspect, the second illumination light beam may be diverging light that spreads out in a substantially right-circular-cone shape, and the endoscope system may be provided with an inclination-direction detecting portion that detects a direction in which the imaging subject is inclined with respect to the distal end of the inserted portion on the basis of a distribution of brightness in the area illuminated by the second illumination light beam in the image acquired by the image-acquisition portion.

In the above-described first aspect, the image-acquisition portion may be configured such that an angle of view thereof can be changed between a first angle of view and a second angle of view that is smaller than the first angle of view.

In the above-described invention, the illumination device may be provided in such a way that a position thereof in a longitudinal direction in the channel can be changed.

In the above-described first aspect, the second illuminating portion may be configured such that a direction in which the second illumination light beam is emitted can be changed.

A second aspect of the present invention is an illumination device including: an illuminating portion that can be inserted into a channel, which is provided in an inserted portion of an endoscope and passes therethrough in a longitudinal direction thereof, and that emits an illumination light beam from a distal end; a long, thin pulling member that is connected to a base end of the illuminating portion and that has a greater length than the length of the channel; and a positioning member that sets a position of the illuminating portion in the channel, wherein the illuminating portion emits the illumination light beam that has a smaller divergence angle than that of an illumination light beam emitted from an illuminating portion provided in the inserted portion and for Which an image-acquisition portion provided in the inserted portion has sensitivity, and the positioning member performs positioning so that the illuminating portion can be removed from the channel by pulling the pulling member.

BRIEF DESCRIPTION OF DRAWINGS

FIG. 6 is a diagram showing another modification of the endoscope system in FIG. 1.

DESCRIPTION OF EMBODIMENT

An endoscope system according to an embodiment of the present invention will be described below with reference to the drawings.

Figure 1:
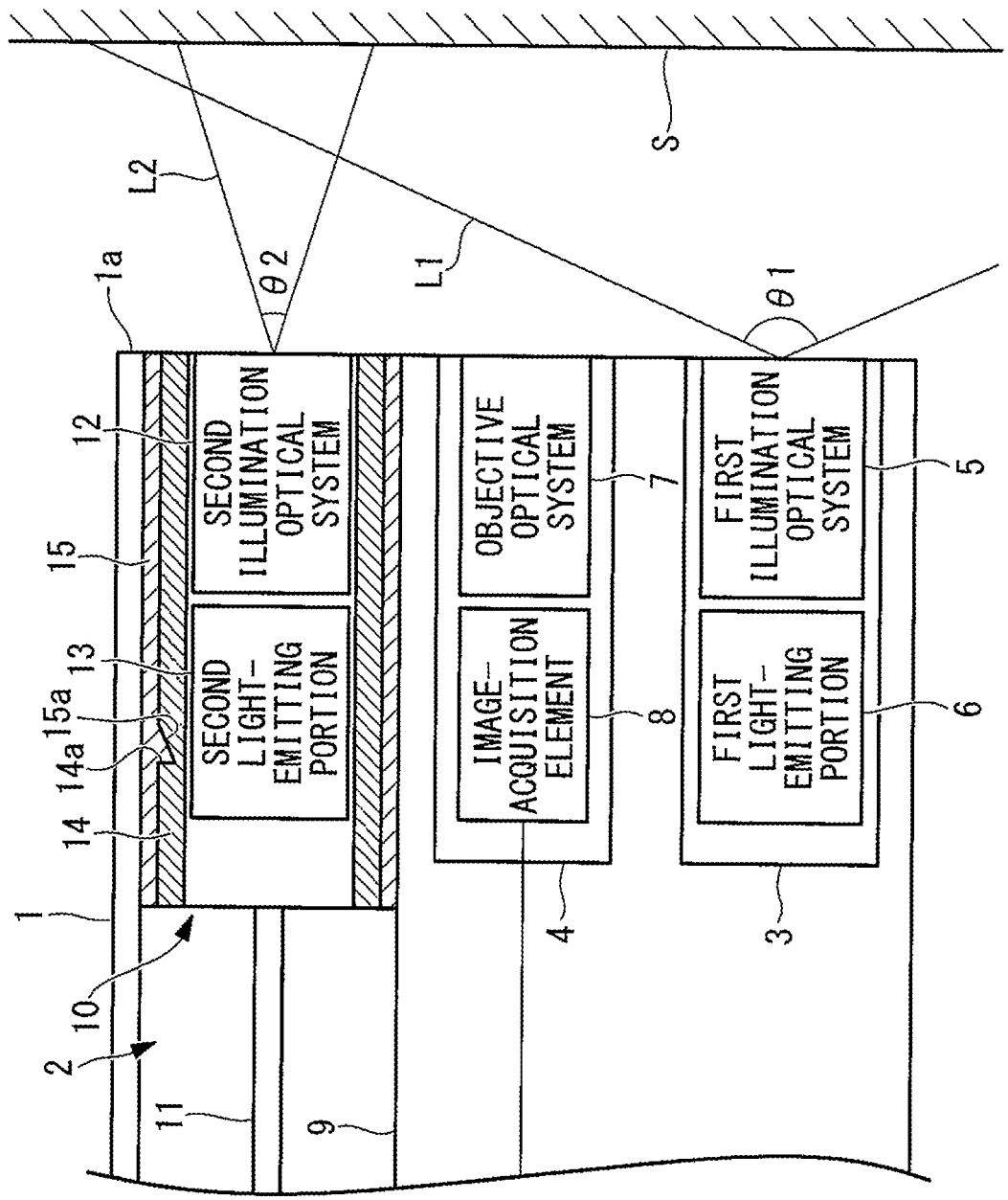
FIG. 1 is a diagram showing the configuration of a distal-end portion of an inserted portion of an endoscope system according to a first embodiment of the present invention.

As shown in FIG. 1, the endoscope system according to this embodiment is provided with an endoscope including a long, thin inserted portion 1 that can be inserted into a body and an illumination device 2 inserted into the inserted portion 1.

The inserted portion 1 of the endoscope is a scope portion of the endoscope having a cylndricaj hollow structure and is provided with, in a distal-end portion thereof, a first illuminating portion 3 from which a first illumination light beam L1 is emitted forward with respect to a distal end 1a of the inserted portion 1 and an image-acquisition portion 4 that acquires an image of an imaging subject S facing the distal end 1a of the inserted portion 1.

The first illuminating portion 3 is provided with a first illumination optical system 5 that is disposed at the distal end 1a of the inserted portion 1 and a first light-emitting portion 6 that is disposed on the base-end side of the first illumination optical system 5 and that emits the first illumination light beam L1 toward the first illumination optical system 5.

The first illumination optical system 5 causes the first illumination light beam L1 that has entered from the first light-emitting portion 6 to diverge to irradiate the imaging subject S. Here, the first illumination light beam L1 emitted from the first illumination optical system 5 has a divergence angle $\theta 1$ that is larger than the angle of view of an objective optical system 7 so that the entire viewing field of the objective optical system 7 can be illuminated by the first illumination light beam L1.

The first light-emitting portion 6 is, for example, a light guiding member, such as a light guide that is disposed in the inserted portion 1 along the longitudinal direction thereof, and is configured so as to guide, to the distal end thereof, the first illumination light beam L1, such as white light that comes from a light source that is disposed outside the inserted portion 1 and that enters from the base end thereof, and to emit the first illumination light beam L1 from the distal end. Alternatively, the first light-emitting portion 6 may be a light-emitting element such as an LED or an LD, or a light-guiding member.

The image-acquisition portion 4 is provided with the objective optical system 7 that is disposed at the distal end 1a of the inserted portion 1 and an image-acquisition element 8 that is disposed on the base-end side of the objective optical system 7.

The objective optical system 7 forms an image of light that comes from the imaging subject S and that enters the objective optical system 7.

The image-acquisition element 8 is, for example, a CCD image sensor or a CMOS image sensor, in which an image-acquisition surface thereof is disposed at an imaging surface of the objective optical system 7, and acquires an optical image of the imaging subject S formed by the objective optical system 7. The endoscope image of the imaging subject S acquired by the image-acquisition element 8 is displayed on a display (not shown).

The inserted portion 1 is additionally provided with a channel 9 that passes therethrough in the longitudinal direction and into which an endoscope treatment tool can be inserted.

The illumination device 2 is provided with a second illuminating portion 10 and a pulling member 11 that is connected to the base end of the second illuminating portion 10, and is inserted into the channel 9.

The second illuminating portion 10 is provided with: a second illumination optical system 12; a second light-emitting portion 13 that is disposed on the base-end side of the second illumination optical system 12; and an outer cylinder 14 that holds the second illuminating portion 10 and the second light-emitting portion 13 in the interior thereof.

The second illumination optical system 12 causes a second illumination light beam L2 that has entered from the second light-emitting portion 13 to diverge to irradiate the imaging subject S. Here, the second illumination light beam L2 emitted from the second illumination optical system 12 has a divergence angle $\theta 2$ that is smaller than the angle of view of the objective optical system 7 so that only a portion of the viewing field of the objective optical system 7 can be illuminated by the second illumination light beam L2.

The second light-emitting portion 13 is, for example, a light guiding member, such as a light guide, a light-emitting element, such as an LED or an LD, or a light-guiding member, and emits the second illumination light beam L2 toward the second illumination optical system 12. The second illumination light beam L2 is visible light such as white light.

The pulling member 11 is a long, thin member, such as a coil wire, that has, while possessing flexibility, a moderate rigidity that allows a motion imparted to the base end thereof to be transmitted to the distal end thereof. The pulling member 11 has a greater longitudinal dimension than the longitudinal dimension of the channel 9, and the base-end portion of the pulling member 11 extends to outside the inserted portion 1 from the base end of the channel 9.

The outer cylinder 14 is a cylindrical member that has an outer diameter that is smaller than the inner diameter of the channel 9, and, on the outer circumferential surface thereof, a groove 14a into which a protrusion 15a of a positioning member 15, described later, can be inserted in a radial direction is formed.

The illumination device 2 is additionally provided with the positioning member 15 for temporarily securing the second illuminating portion 10 to an inner wall of the channel 9. The positioning member 15 is a circular cylindrical member that has an outer diameter that is substantially equal to the inner diameter of the channel 9, and is fitted in the channel 9. The positioning member 15 is secured to the inner wall of the channel 9 by means of friction between an inner circumferential surface of the channel 9 and an outer circumferential surface of the positioning member 15.

The positioning member 15 has the protrusion 15a that protrudes radially inward on the inner circumferential surface. When the protrusion 15a enters the groove 14a, the second illuminating portion 10 is positioned, inside the channel 9, in the longitudinal direction of the channel 9. The protrusion 15a is formed of a material that, when the second illuminating portion 10 is pulled toward the base end, allows the protrusion 15a to be dislodged from the groove 14a by being elastically deformed by receiving a force from the second illuminating portion 10. The protrusion 15a has a shape that is inclined toward the base end from the distal end so that the protrusion 15a is easily dislodged from the groove 14a when the second illuminating portion 10 is pulled toward the base end.

Figure 2:
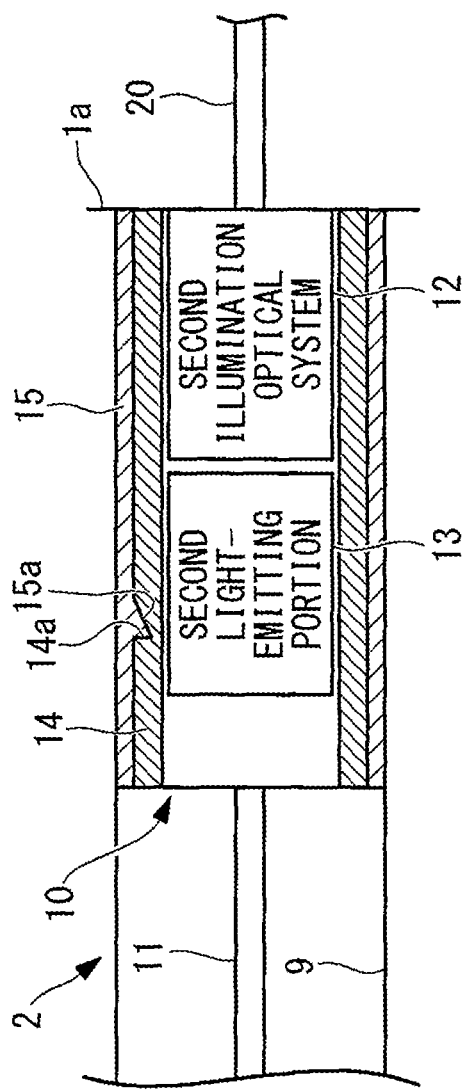
FIG. 2 is a diagram for explaining a method of attaching an illumination device in FIG. 1 inside a channel.

FIG. 2 shows the procedure for attaching the illumination device 2 inside the channel 9. To attach the illumination device 2, an insertion pulling member 20, such as a wire, that is connected to the distal end of the second illuminating portion 10 is used. First, the positioning member 15 is inserted into the channel 9 from the distal-end side of the channel 9 and is disposed in the distal-end portion of the channel 9. Next, the illumination device 2 is inserted, with the insertion pulling member 20 at the leading position, into the channel 9 from the base-end side thereof. Next, the insertion pulling member 20, which protrudes from an opening of the channel 9 at a surface at the distal end 1a of the inserted portion 1, is pulled, and the illumination device 2 is pulled toward the distal end until reaching a position at which the protrusion 15a of the positioning member 15 is fitted into the groove 14a of the outer cylinder 14. By doing so, the illumination device 2 can be attached inside the channel 9. After attaching the illumination device 2, the insertion pulling member 20 is removed.

Next, the operation of the thus-configured endoscope system will be described.

In order to observe and treat the body interior by using the endoscope system according to this embodiment, for example, the inserted portion 1 is inserted into the lower digestive tract from the anus, and the inserted portion 1 is moved forward in the lower digestive tract. In the process of insertion, the second illumination light beam L2 is emitted from the second illuminating portion 10. Inside the tubular lower digestive tract, the second illumination light beam L2, which has a small divergence angle θ2, reaches far from the distal end 1a of the inserted portion 1, and thus, it is possible to brightly illuminate a far viewing field. Therefore, an operator can gain, on the basis of an endoscope image, a sense of distance to the imaging subject S that is positioned forward in the direction in which the inserted portion 1 is inserted, and thus, he/she can accurately perform manipulation for inserting the inserted portion 1.

After the inserted portion 1 is inserted until reaching a position of an affected portion in the lower digestive tract, by pulling the base-end portion of the pulling member 11 extending to outside the inserted portion 1 from the base end of the channel 9, the second illuminating portion 10 is removed from the positioning member 15, and thus, the second illuminating portion 10 and the pulling member 11 are removed from the channel 9. By doing so, only the positioning member 15 is left in the channel 9. Next, a treatment tool to be used for treating the affected portion is inserted into the channel 9, and the affected portion is treated by using the treatment tool. At this time, the first illumination light beam L1 is emitted from the first illuminating portion 3. When treating the affected portion, the distal end 1a of the inserted portion 1 is brought close to the affected portion, and the affected portion is observed in detail. Therefore, the entire viewing field of the objective optical system 7 is brightly illuminated by the first illumination light beam L1, which has a large divergence angle θ1, and thus, it is possible to clearly observe the affected portion.

As has been described above, with this embodiment, when performing manipulation for inserting the inserted portion 1 into the body, a far viewing field is illuminated by using the second illuminating portion 10 for the narrowly-distributed light, and thus, it is possible to acquire good information about the distance to the imaging subject S that is positioned forward in the insertion direction. After the inserted portion 1 is inserted until reaching the target position in the body, by removing the second illuminating portion 10 from the channel 9, it is possible to use the channel 9 as a treatment tool channel. Note that the observation-distance calculating portion 16 may be configured by combination of a general purpose processor and a program, or a specific integrated circuit, such as ASIC (Application Specific Integrated Circuit) and FPGA (Field-Programmable Gate Array), and a dedicated processor or a combination of one or more of them. In this ways, by using a common space for the illumination device 2, which is needed particularly when inserting the inserted portion 1, and the treatment tool, which is needed after inserting the inserted portion 1, there is an advantage in that it is possible to reduce the diameter of the inserted portion 1.

Figure 3:
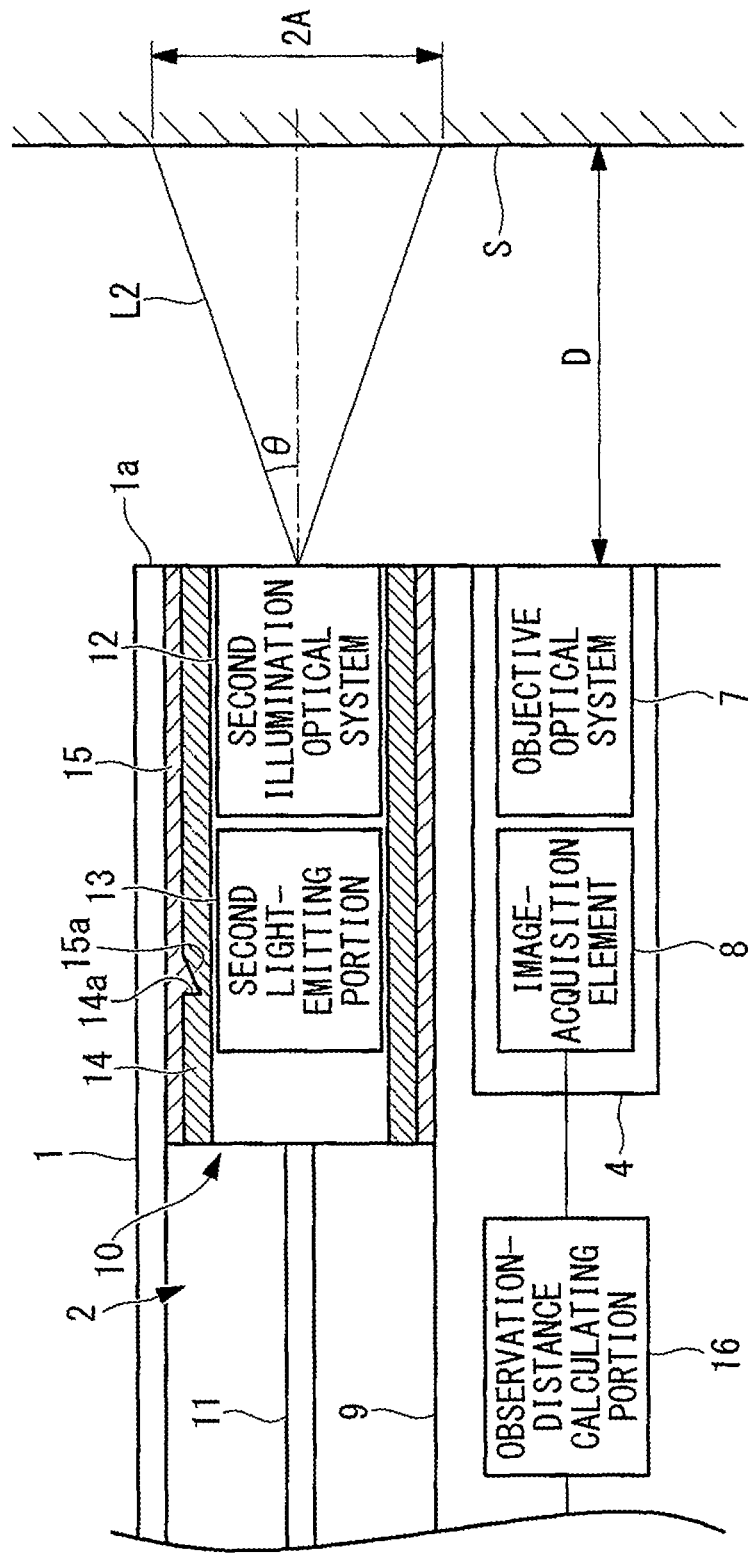
FIG. 3 is a diagram showing a modification of the endoscope system in FIG. 1.

As shown in FIG. 3, in this embodiment, the endoscope may be provided with an observation-distance calculating portion 16 that calculates an observation distance D from the distal end 1a of the inserted portion 1 to the imaging subject S on the basis of the radial dimension of the area illuminated by the second illumination light beam L2 in the endoscope image.

In this case, the second illuminating portion 10 emits the second illumination light beam L2, which diverges in a substantially right-circular-cone shape, toward the imaging subject S. Therefore, the area illuminated by the second illumination light beam L2 on the imaging subject S, which faces the distal end 1a of the inserted portion 1, takes a substantially circular shape. The relationship between a radius A of the illumination area and the observation distance D is expressed by the expression below. In the expression below, θ is ½ of the divergence angle θ2 of the second illumination light beam L2 emitted from the second illumination optical system 12 (an angle formed by the center line and the generatrix in the right-circular-cone shape of the second illumination light beam L2).

$$D = A/\tan \theta$$

The observation-distance calculating portion 16 identifies the area illuminated by the second illumination light beam L2 in the endoscope image acquired by the image-acquisition portion 4, calculates the radius A of the identified illumination area, and calculates the observation distance D on the basis of the above expression by using the calculated radius A. To identify the illumination area in the endoscope image, for example, a region having a luminance value that is equal to or greater than a predetermined threshold is identified. The observation distance D identified by the observation-distance calculating portion 16 is, for example, displayed on the display.

By doing so, it is possible to provide the operator with the observation distance D so as to serve as information for assisting the insertion manipulation.

In a modification in FIG. 3, the second illumination light beam L2 may be light in a non-visible region (non-visible light) instead of the visible light. It suffices that the wavelength of the second illumination light beam L2 be a wavelength for which the image-acquisition element 8 has sensitivity, and, for example, near-infrared light, which has a low influence on biological tissue, is suitable.

In the case in which the second illumination light beam L2 is non-visible light, when inserting the inserted portion 1, the imaging subject S may be illuminated by using the first illumination light beam L1. By doing so also, it is possible to acquire the information about the distance to the far imaging subject S on the basis of the observation distance D acquired by using the second illuminating portion 10 for narrowly-distributed light.

Figure 4:
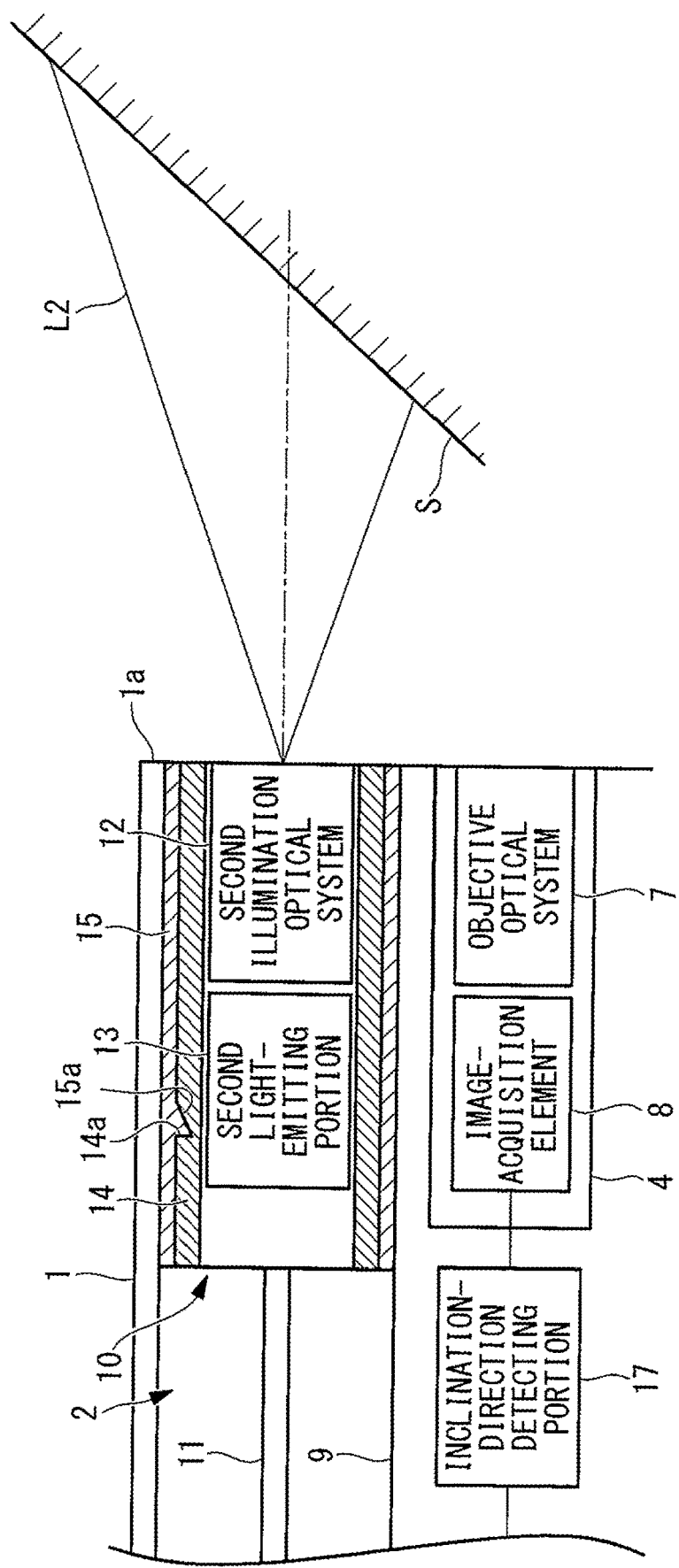
FIG. 4 is a diagram showing another modification of the endoscope system in FIG. 1.

In this embodiment, as shown in FIG. 4, the endoscope may be provided with an inclination-direction detecting portion 17 that detects the direction in which the imaging subject S is inclined with respect to the distal end 1a of the inserted portion 1 on the basis of the distribution of the brightness of the second illumination light beam L2 in the endoscope image. Note that the inclination-direction detecting portion 17 may be configured by combination of a general purpose processor and a program, or a specific integrated circuit, such as ASIC (Application Specific Integrated Circuit) and FPGA (Field-Programmable Gate Array), and a dedicated processor or a combination of one or more of them.

In this modification also, the second illuminating portion 10 emits the second illumination light beam L2, which diffuses in a substantially right-circular-cone shape, toward the imaging subject S.

In the case in which the imaging subject S is inclined with respect to the longitudinal direction of the inserted portion 1, the observation distances differ depending on the positions in the imaging subject S, and the brightness of the second illumination light beam L2 on the imaging subject S decreases with an increase in the observation distances. The inclination-direction detecting portion 17 detects, in the area illuminated by the second illumination light beam L2 in the imaging subject S, the darkest direction as the farthest direction from the distal end 1a of the inserted portion 1. The direction detected by the inclination-direction detecting portion 17 is, for example, displayed on the display. By doing so, it is possible to indicate to the operator the direction in which the inserted portion 1 should be inserted.

Figure 5:
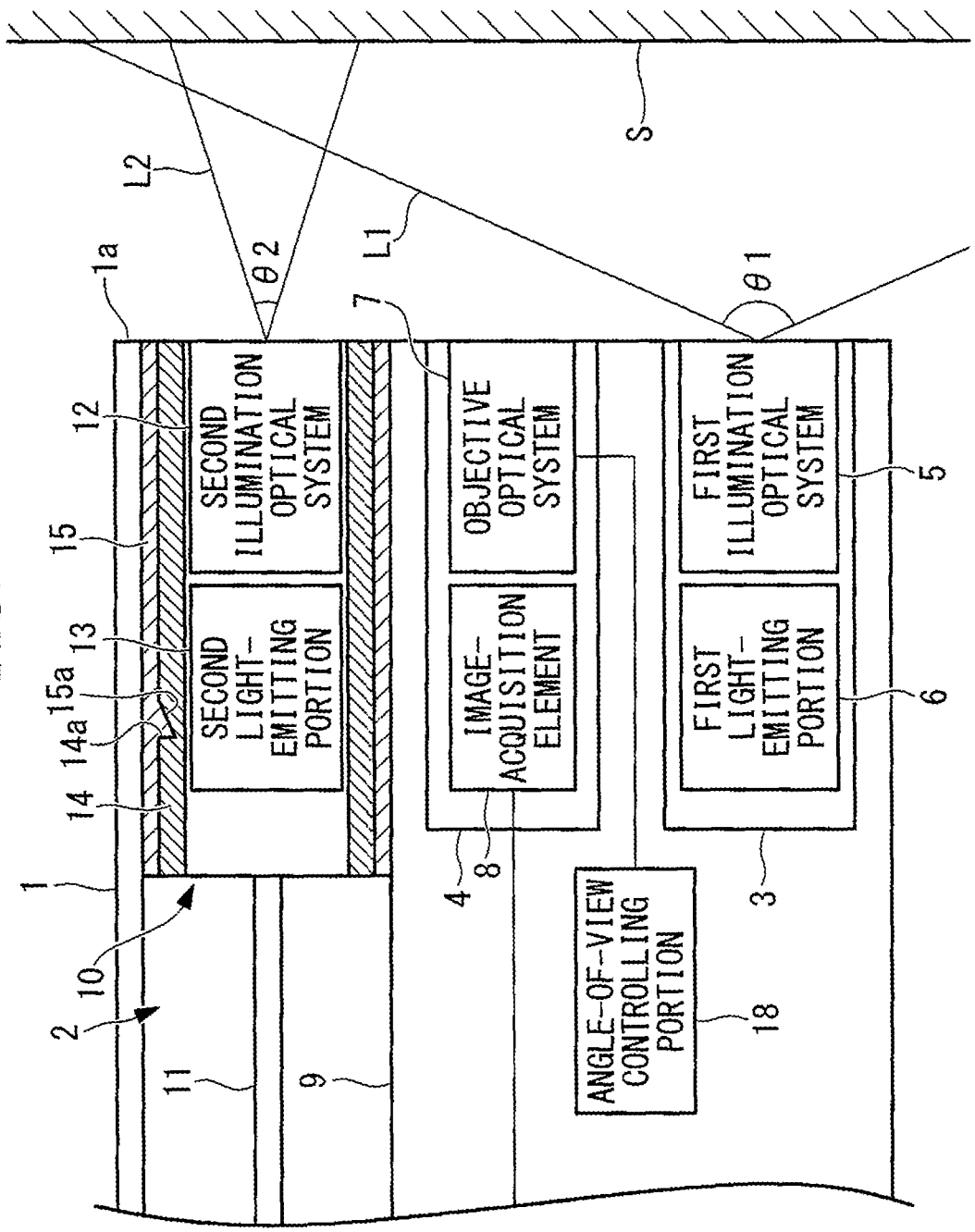
FIG. 5 is a diagram showing another modification of the endoscope system in FIG. 1.

In this embodiment, as shown in FIG. 5, the configuration thereof may be such that the angle of view of the objective optical system 7 can be changed between a first angle of view and a second angle of view, and the endoscope may be provided with an angle-of-view controlling portion 18 that controls the angle of view of the objective optical system 7 depending on which one of the first illumination light beam L1 and the second illumination light beam L2 is radiated onto the imaging subject S. Note that the angle-of-view controlling portion 18 may be configured by combination of a general purpose processor and a program, or a specific integrated circuit, such as ASIC (Application Specific Integrated Circuit) and FPGA (Field-Programmable Gate Array), and a dedicated processor or a combination of one or more of them.

The first angle of view is an angle of view that is suitable for observing the imaging subject S by bringing the distal end 1a of the inserted portion 1 into close proximity to the imaging subject S, and is larger than the divergence angle θ1 of the first illumination light beam L1. The second angle of view is an angle of view that is suitable for observing the area illuminated by the second illumination light beam L2, and is smaller than the first angle of view and larger than the divergence angle θ2 of the second illumination light beam L2.

The angle-of-view controlling portion 18 sets the angle of view of the objective optical system 7 to the first angle of view when the second illumination light beam L2 is not being emitted from the second illumination optical system 12, and sets the angle of view of the objective optical system 7 to the second angle of view when the second illumination light beam L2 is being emitted from the second illumination optical system 12.

By doing so, when observing and treating the affected portion, the angle of view of the objective optical system 7 is set to a wide angle, and thus, it is possible to acquire an image of a large area; and, when inserting the inserted portion 1, the angle of view of the objective optical system 7 is set to a narrow angle, and thus, it is possible to prevent needless acquisition of an image of a portion that is not illuminated by the second illumination light beam L2.

In this embodiment, as shown in FIG. 6, the second illuminating portion 10 may be provided so as to be movable in the channel 9 in the longitudinal direction of the inserted portion 1.

By disposing the second illuminating portion 10 at a position that is protruded farther out from the distal end 1a of the inserted portion 1, it is possible to illuminate a farther imaging subject S with the second illumination light beam L2.

In this embodiment, as shown in FIG. 6, the configuration thereof may be such that the direction in which the second illuminating portion 10 emits the second illumination light beam L2 can be changed, and the endoscope may be provided with an illumination controlling portion 19 that controls the direction in which the second illumination light beam L2 is emitted from the second illuminating portion 10. Note that the illumination controlling portion 19 may be configured by combination of a general purpose processor and a program, or a specific integrated circuit, such as ASIC (Application Specific Integrated Circuit) and FPGA (Field-Programmable Gate Array), and a dedicated processor or a combination of one or more of them.

By doing so, for example, by changing the emitting direction of the second illumination light beam L2 in accordance with the curved shape of the lumen, it is possible to reliably illuminate a deeper portion of the lumen in the curved lumen by using the second illumination light beam L2.

As a result, the following aspect is read by the above described embodiment of the present invention.

A first aspect of the present invention is an endoscope system including: a long, thin inserted portion that includes a first illuminating portion that emits a first illumination light beam toward an imaging subject, an image-acquisition portion that acquires an image of the imaging subject, and a channel that passes therethrough in a longitudinal direction; and an illumination device that includes a second illuminating portion that is disposed in the channel and that emits a second illumination light beam toward the imaging subject, and a long, thin pulling member that is connected to a base end of the second illuminating portion and that extends to outside from a base end of the channel, wherein the second illuminating portion is provided in such a way that the second illuminating portion can be removed from the channel by pulling the pulling member, and emits the second illumination light beam, which has a divergence angle that is smaller than that of the first illumination light beam and for which the image-acquisition portion has sensitivity.

With the first aspect of the present invention, an image of the imaging subject that is illuminated by the first illumination light beam emitted from the first illuminating portion is acquired by the image-acquisition portion, and thus, it is possible to acquire an image of the imaging subject.

In this case, the second illumination light beam, which has a divergence angle that is smaller than that of the first illumination light beam, reaches farther than the first illumination light beam, and thus, an image of a far imaging subject being irradiated with the second illumination light beam is acquired by the image-acquisition portion. Therefore, on the basis of the image acquired in a state in which the second illumination light beam is being radiated, it is possible to acquire information about the distance from the distal end of the inserted portion to the far imaging subject.

After the inserted portion is inserted until reaching a desired position, by removing the illumination device from the channel by pulling the pulling member, it is possible to use the channel as a channel for introducing a treatment tool to the distal-end side of the inserted portion. In this way, by using a common space so as to serve as the channel for the second illumination device and the treatment tool, which are selectively used, it is possible to reduce the diameter of the inserted portion.

In the above-described first aspect, the second illumination light beam may be visible light.

By doing so, because a visible-light image of a far imaging subject is acquired by the image-acquisition portion, it is possible to provide an operator with the visible-light image so as to serve as information for assisting manipulation for inserting the inserted portion.

In the above-described first aspect, the second illumination light beam may be non-visible light.

By doing so, an image acquired by the image-acquisition portion does not display a reflected-light image based on the second illumination light beam. Therefore, when manipulating the inserted portion also, it is possible to provide the operator with a normal image of the imaging subject that is illuminated by the first illumination light beam.

In the above-described first aspect, the second illumination light beam may be diverging light that spreads out in a substantially right-circular-cone shape, and the endoscope system may be provided with an observation-distance calculating portion that calculates an observation distance from a distal end of the inserted portion to the imaging subject on the basis of the size of an area illuminated by the second illumination light beam in the image acquired by the image-acquisition portion.

Because the dimension of the area illuminated by the second illumination light beam on the imaging subject is proportional to the distance from the distal end of the inserted portion to the imaging subject, it is possible to obtain the observation distance on the basis of the dimension of the area illuminated by the second illumination light beam.

In the above-described first aspect, the second illumination light beam may be diverging light that spreads out in a substantially right-circular-cone shape, and the endoscope system may be provided with an inclination-direction detecting portion that detects a direction in which the imaging subject is inclined with respect to the distal end of the inserted portion on the basis of a distribution of brightness in the area illuminated by the second illumination light beam in the image acquired by the image-acquisition portion.

Because the contrast of the second illumination light beam on the imaging subject depends on the distance from the distal end of the inserted portion to the imaaing subject, it is possible to detect the direction in which the imaging subject is inclined with respect to the distal end of the inserted portion on the basis of the distribution of the brightness in the area illuminated by the second illumination light beam.

In the above-described first aspect, the image-acquisition portion may be configured such that an angle of view thereof can be changed between a first angle of view and a second angle of view that is smaller than the first angle of view.

By doing so, by setting the angle of view of the image-acquisition portion to the first angle of view when performing observation by illuminating the imaging subject by the first illumination light beam and by setting the angle of view of the image-acquisition portion to the second angle of view when performing observation by illuminating the imaaing subject by the second illumination light beam, it is possible to change the image-acquisition area of the image-acquisition portion in accordance with the area illuminated by the illumination light beam.

In the above-described invention, the illumination device may be provided in such a way that a position thereof in a longitudinal direction in the channel can be changed.

By doing so, by disposing the second illuminating portion farther on the distal-end side, the second illumination light beam reaches a farther imaaing subject. By doing so, it is possible to acquire information about the distance to the farther imaging subject.

In the above-described first aspect, the second illuminating portion may be configured such that a direction in which the second illumination light beam is emitted can be changed.

By doing so, by changing the direction in which the second illumination light beam is emitted in accordance with the direction in which the inserted portion is inserted or the like, it is possible to acquire information about the distances to different positions in the far imaging subject.

A second aspect of the present invention is an illumination device including: an illuminating portion that can be inserted into a channel, which is provided in an inserted portion of an endoscope and passes therethrough in a longitudinal direction thereof, and that emits an illumination light beam from a distal end; a long, thin pulling member that is connected to a base end of the illuminating portion and that has a greater length than the length of the channel; and a positioning member that sets a position of the illuminating portion in the channel, wherein the illuminating portion emits the illumination light beam that has a smaller divergence angle than that of an illumination light beam emitted from an illuminating portion provided in the inserted portion and for which an image-acquisition portion provided in the inserted portion has sensitivity, and the positioning member performs positioning so that the illuminating portion can be removed from the channel by pulling the pulling member.

REFERENCE SIGNS LIST

1 inserted portion
2 illumination device
3 first illuminating portion
4 image-acquisition portion
5 first illumination optical system
6 first light-emitting portion
7 objective optical system
8 image-acquisition element
9 channel
10 second illuminating portion
11 pulling member
12 second illumination optical system
13 second light-emitting portion
14 outer cylinder
14*a* groove
15 positioning member
15*a* protrusion
16 observation-distance calculating portion
17 inclination-direction detecting portion
18 angle-of-view controlling portion
19 illumination controlling portion

The invention claimed is:

1. An endoscope system comprising:
an inserted portion that includes a first illuminating portion that emits a first illumination light beam toward an imaging subject, an image-acquisition portion that acquires an image of the imaging subject, and a channel that passes therethrough in a longitudinal direction;
an illumination device that includes a second illuminating portion that is insertable in the channel and that emits a second illumination light beam toward the imaging subject, and a pulling member that is connected to a base end of the second illuminating portion and that extends to outside from a base end of the channel; and a protrusion that is fixed to an inner circumferential surface of the channel, wherein the second illuminating portion is fixed at a predetermined position in the channel by a part of an outer circumferential surface of the second illuminating portion contacting the protrusion, and emits the second illumination light beam, which has a divergence angle that is smaller than that of the first illumination light beam and for which the image-acquisition portion has sensitivity, and wherein the protrusion has elasticity.

2. An endoscope system according to claim 1, wherein the second illumination light beam is visible light.

3. An endoscope system according to claim 1, wherein the second illumination light beam is non-visible light.

4. An endoscope system according to claim 1,
wherein the second illumination light beam is diverging light that spreads out in a substantially right-circular-cone shape, and
the endoscope system is provided with a processor that calculates an observation distance from a distal end of the inserted portion to the imaging subject on the basis of the size of an area illuminated by the second illumination light beam in the image acquired by the image-acquisition portion.

5. An endoscope system according to claim 1,
wherein the second illumination light beam is diverging light that spreads out in a substantially right-circular-cone shape, and
the endoscope system is provided with a processor that detects a direction in which the imaging subject is inclined with respect to the distal end of the inserted portion on the basis of a distribution of brightness in the area illuminated by the second illumination light beam in the image acquired by the image-acquisition portion.

6. An endoscope system according to claim 1, wherein the illumination device is provided in such a way that a position thereof in a longitudinal direction in the channel can be changed.

7. An endoscope system according to claim 1, wherein the second illuminating portion is configured such that a direction in which the second illumination light beam is emitted can be changed.

8. An endoscope system according to claim 1,
wherein the protrusion is integrally formed with an inner cylinder that has an outer diameter substantially equal to an inner diameter of the channel, the inner cylinder is fixed in the inner circumferential surface of the channel,
wherein the second illuminating portion can be fixed to the inner circumferential surface of the channel with the protrusion.

9. An endoscope system according to claim 1,
wherein the protrusion protrudes toward an inner side of the channel.

10. An endoscope system according to claim 1,
wherein the second illuminating portion has a groove on the outer circumferential surface thereof into which the protrusion can be fitted.

11. An endoscope system according to claim 10,
wherein the groove is integrally formed with an outer cylinder that has an outer diameter substantially equal to the inner diameter of an inner cylinder, the outer cylinder is fixed in the outer circumferential surface of the second illumination device.

12. An illumination device comprising:
an illuminating portion that can be inserted into a channel, which is provided in an inserted portion of an endoscope and passes therethrough in a longitudinal direction thereof, and that emits an illumination light beam from a distal end;
a pulling member that is connected to a base end of the illuminating portion and that has a greater length than the length of the channel; and
a cylindrical member that has an outer diameter that is substantially equal to an inner diameter of the channel, and that sets a position of the illuminating portion in the channel,
wherein the illuminating portion emits the illumination light beam that has a smaller divergence angle than that of an illumination light beam emitted from an illuminating portion provided in the inserted portion and for which an image-acquisition portion provided in the inserted portion has sensitivity, and
the cylindrical member performs positioning so that the illuminating portion can be removed from the channel by pulling the pulling member.

13. An endoscope system comprising an endoscope having an inserted portion that includes a channel that passes therethrough in a longitudinal direction and an illumination device that can be inserted into a channel,
the illumination device comprising:
an illuminating portion that can be inserted into a channel, and that emits an illumination light beam from a distal end; and
a pulling member that is connected to a base end of the illuminating portion and that has a greater length than the length of the channel,
wherein the illuminating portion is fixed at a predetermined position in the channel by a part of an outer circumferential surface of the illuminating portion contacting a protrusion fixed to an inner circumferential surface of the channel, and emits the illumination light beam that has a smaller divergence angle than that of an illumination light beam emitted from an illuminating portion provided in the inserted portion and for which an image-acquisition portion provided in the inserted portion has sensitivity, and
wherein the protrusion has elasticity.

14. An endoscope system according to claim 13,
wherein the protrusion is integrally formed with an inner cylinder that has an outer diameter substantially equal to an inner diameter of the channel, the inner cylinder is fixed in the inner circumferential surface of the channel,
wherein the illuminating portion can be fixed to the inner circumferential surface of the channel with the protrusion.

15. An endoscope system according to claim 13,
wherein the protrusion protrudes toward an inner side of the channel.

16. An endoscope system according to claim 13,
wherein the illuminating portion has a groove on the outer circumferential surface thereof into which the protrusion can be fitted.

17. An endoscope system according to claim 16,
wherein the groove is integrally formed with an outer cylinder that has an outer diameter substantially equal to the inner diameter of an inner cylinder, the outer cylinder is fixed in the outer circumferential surface of the illumination device.

\* \* \* \* \*